United States Patent
Birmingham et al.

(10) Patent No.: US 6,291,699 B1
(45) Date of Patent: Sep. 18, 2001

(54) 2-ALKYL-4-(2,6-DIALKYLPHENYL) INDENES

(75) Inventors: John M. Birmingham, Longmont; Sandra Russo-Rodriguez, Superior, both of CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 09/379,803

(22) Filed: Aug. 24, 1999

(51) Int. Cl.[7] .............................. C07F 7/08; C07F 17/00; B01J 31/00; C07C 13/15

(52) U.S. Cl. ............................ 556/489; 556/11; 556/12; 556/28; 556/53; 556/465; 502/103; 502/117; 502/155; 526/127; 526/160; 526/351; 526/943; 585/25; 585/26; 585/27

(58) Field of Search ................................. 556/11, 12, 28, 556/53, 465, 489; 502/103, 117, 155; 526/127, 160, 351, 943; 585/27, 26, 25

(56) References Cited

U.S. PATENT DOCUMENTS 5,753,769 * 5/1998 Ueda et al. ........................ 525/323
5,770,753 * 6/1998 Kuber et al. ........................ 556/11

* cited by examiner

*Primary Examiner*—Porfirio Nazario-Gonzalez
(74) *Attorney, Agent, or Firm*—Edward S. Irons

(57) ABSTRACT

2-alkyl-4-(2,6-dialkylphenyl) indenes, methods for the synthesis thereof, methods for converting such indenes to bridged metallocene ligands, methods for converting such ligands to bridged metallocenes and olefin polymerization processes in which such metallocenes are used as a catalyst or as a component of a catalyst system are described.

22 Claims, No Drawings

2-ALKYL-4-(2,6-DIALKYLPHENYL) INDENES

FIELD OF THE INVENTION

This invention relates to 2-alkyl-4-(2,6-dialkylphenyl) indenes, to the synthesis of said indenes, and to metallocene compounds including olefin polymerization catalysts derived therefrom.

BACKGROUND OF THE INVENTION

Unbridged and bridged substituted cyclopentadienyl and indenyl metallocene olefin polymerization catalysts are known. Particular substituted indenes useful as metallocene ligands have been synthesized by cross-coupling reactions. See *J.Org.Chem.* (1984) 99:4226–7 and U.S. Pat. No. 5,789, 634.

SUMMARY OF THE INVENTION

One aspect of this invention provides 2-alkyl-4-(2,6-dialkylphenyl) indenes. Another aspect of the invention may comprise methods, including cross-coupling reactions, for the synthesis of such indenes.

A specific embodiment of the invention may comprise cross-coupling conversion of a 2-alkyl-4X indene (X=halogen or triflate) to a 2-alkyl-4-(2,6-dialkylphenyl) indene.

The invention may also comprise treating 2-alkyl-4-(2,6-dialkylphenyl) indene with a bridging reagent to provide a bridged compound useful as a metallocene ligand.

A specific aspect of the invention comprises conversion of the compounds to the corresponding bridged metallocenes. The invention also includes use of such bridged metallocenes per se or in conjunction with a cocatalyst, such as aluminoxane, as olefin polymerization catalysts and the olefin polymers so produced.

DEFINITIONS

Cross-Coupling Reaction: Any reaction of an organometallic compound $\underline{R}$—$\underline{M}$ with an organic compound $\underline{R}^1$—$\underline{X}$, wherein $\underline{R}$ and $\underline{R}^1$ are the same or different organic groups and $\underline{X}$ is a leaving group to give a product $\underline{R}$—$\underline{R}^1$. In the context of the invention, $\underline{R}^1$—$\underline{X}$ is a 2-alkyl-4—$\underline{X}$ indene in which $\underline{X}$ is a halogen or triflate.

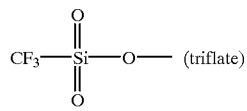

DETAILED DESCRIPTION OF THE INVENTION

1. The 2-Alkyl-4-(2,6-Dialkylphenyl) Indenes

The 2-alkyl-4-(2,6-dialkylphenyl) indenes of this invention have the Formula I:

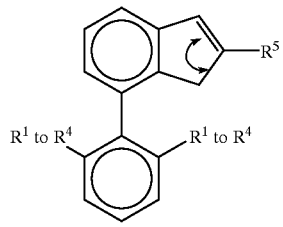

in which $R^1$, $R^2$, $R^3$, $R^4$, and $R^5$ are identical or different hydrocarbyl groups, preferably a $C_1$ to $C_6$ alkyl group or a $C_6$ to $C_{10}$ aryl (Ar), preferably phenyl, group which aryl group may be substituted at any available ring position preferably by a $C_1$ to $C_6$ alkyl group, and in which the symbol z,900 indicates a shift in the position of the double bond. Preferably, due to potential synthesis difficulties, only 1 of $R^1$ to $R^4$ is aryl. No like constraint applies to $R^5$.

2-alkyl-4-phenyl indenes may be synthesized in known manner, e.g., U.S. Pat. No. 5,789,634 (reaction of 2-alkyl-4-chloro indenes with aryl magnesium halides) and *J.Org.Chem.* (1984) 99:4226-7 (nickel catalyzed coupling of 4-bromo indene with phenyl Grignard) or by a cross-coupling reaction, illustrated by Equation 1, in which the $R^1$ $\underline{X}$ reactant is 2-alkyl-4$\underline{X}$ indene, wherein $\underline{X}$=halogen or triflate and the $\underline{R}$—$\underline{M}$ reactant is Equation 1

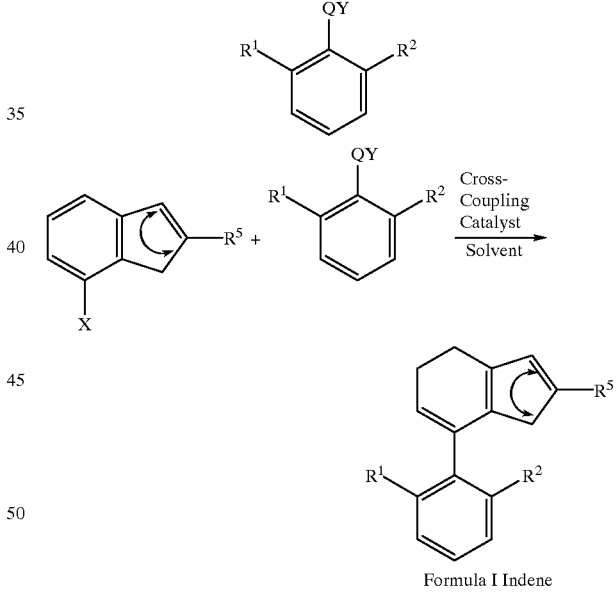

Formula I Indene

In Equation 1, $R^1$ to $R^5$ and z,900 are as described, $\underline{X}$ is any halogen or triflate, and QY is an organometallic substituent in which Q is magnesium, boron, tin, silicon or zinc, and Y may be any X or a $C_1$ to $C_6$ trialkyl tin, a $C_1$ to $C_6$ trialkyl silicon or a phenyl boronic group or —ZnX.

The cross-coupling catalysts useful in the invention may comprise metal, preferably nickel or palladium, compounds having phosphine ligands. Typical cross-coupling catalysts include Ni(dppp)Cl$_2$ (nickel diphenylphosphino propane dichloride), Ni(PPh$_3$)$_2$Cl$_2$, Pd(PPh$_3$)$_4$, X$_2$Pd(PPh$_3$)$_2$ (X=halogen), Cl$_2$Pd(dppf) (dichloro palladium diphenylphosphino ferrocene) or combination of Pd(OAc)$_2$ (palladium acetate) or Pd$_2$dba$_3$ (in which dba is dibenzylidene acetone) with phosphine $PR_3$, $PAr_3$, or $PR_2Ar$ where R is a $C_1$ to $C_6$ alkyl group and Ar is a $C_6$ to $C_{10}$ aryl group.

Useful solvents include ethers, typically diethyl ether, tetrahydrofuran, dioxane and dimethoxyethane or aromatic hydrocarbons, typically benzene, toluene or xylenes.

Preferred conditions, which may be determined in known manner for a specific cross-coupling reaction, are a function of steric hindrance, the specific solvents used, the presence of other reactants including other ligands, and the presence of bases or reducing agents.

The Formula I indene compound may be isolated from the cross-coupling reaction mixture in known manner or further processed in situ.

2. Conversion of Formula I Indenes to Bridged Ligands

As shown by Equation 2, a bridged ligand of Formula II is produced by deprotonation of a Formula I indene with an alkali metal alkyl, followed by reaction of the metallide with an appropriate bridging reagent:

Equation 2

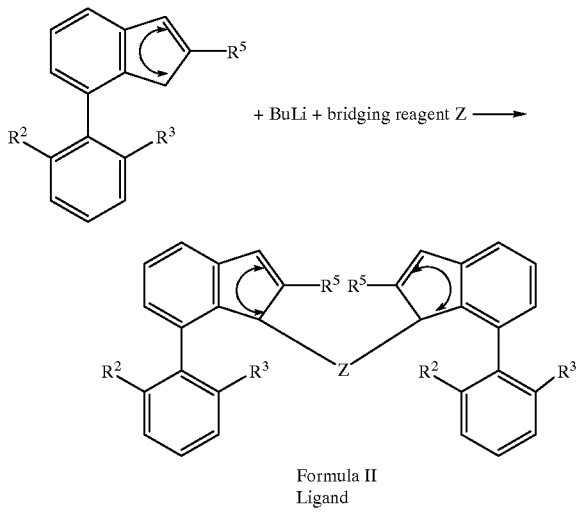

Formula II
Ligand

In Formula I, $R^1$ to $R^5$ are as described and Z is a bridge or linking group. Bridging agents which may be used in the invention are described in U.S. Pat. No. 5,831,105, col. 3, 11. 30–62, which is incorporated herein and made a part of this specification by reference.

Specifically, for silyl bridging, the metal salt of the deprotonated Formula I indene may be treated with a dialkyldihalosilane, preferably dimethyldichlorosilane.

For hydrocarbon bridging, the Formula I indene may be treated with a dihaloalkane or with a dimethylfulvene derivative of a Formula I indene to yield the dimethylcarbon bridged analog.

3. Conversion of Bridged Formula II Ligands to Metallocenes

Formula II ligands may be converted to bridged metallocenes by any of the various methods known to the prior art, e.g., U.S. Pat. Nos. 5,017,714; 5,576,260 (Col. 9, 1. 14 et seq.); 5,616,747 and 5,831,105 and references cited therein. Equation 3 illustrates one such conversion:

Equation 3

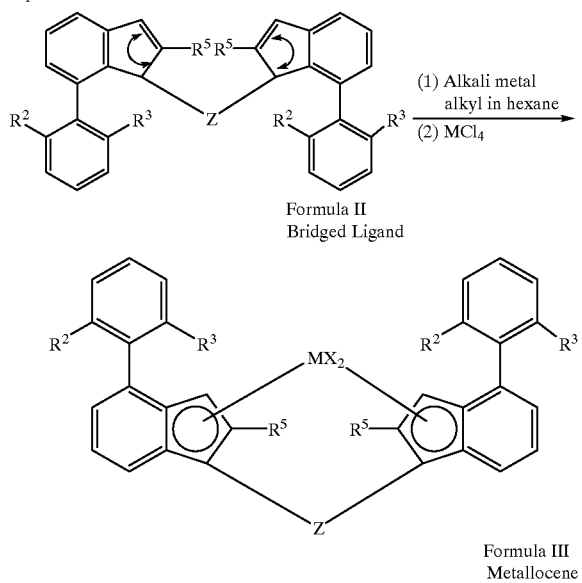

Formula II
Bridged Ligand

Formula III
Metallocene

In Equation 3, $R^1$ to $R^5$, X and Z are as described; M typically is a Group IVA metal, preferably Zr, Ti or Hf. Preferably the alkali metal alkyl is a butyl lithium.

Cocatalyst

The cocatalyst used with a Formula III metallocene is preferably an aluminoxane which may be of the Formula V for the linear type:

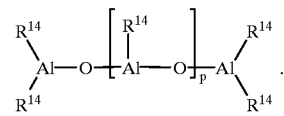

V or Formula VI for the cyclic type:

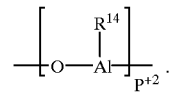

VI

In the Formulae V and VI, the radicals $R^{14}$ may be identical or different and are a $C_1$–$C_6$ alkyl group, a $C_6$–$C_{18}$ aryl group, benzyl or hydrogen, and p is an integer from 2 to 50, preferably from 10 to 35.

The radicals $R^{14}$ are preferably identical and are preferably methyl, isobutyl, phenyl or benzyl, particularly preferably methyl. If the radicals $R^{14}$ are different, they are preferably methyl and hydrogen or, alternatively, methyl and isobutyl, where hydrogen and isobutyl are preferably present to the extent of 0.1–40% (number of radicals $R^{14}$).

The aluminoxane can be prepared in various ways by known processes. One of the methods is, for example, to react an aluminum hydrocarbon compound and/or a hydridoaluminum hydrocarbon compound with water (in gas, solid, liquid or bonded form; for example, as water or crystallization) in an inert solvent (such as, for example, toluene). In order to prepare an aluminoxane containing different alkyl groups $R^{14}$ two different trialkylaluminum compounds ($AlR_3+AlR'_3$) corresponding to the desired composition are reacted with water (cf., S. Pasynakiewicz, *Polyhedron* 9:429 (1990) and EPA 302 424).

Regardless of the preparation method, all the aluminoxane solutions have in common a varying content of unreacted aluminum starting compound. The metallocene may be pre-activated by means of an aluminoxane of Formula V or VI before use in the polymerization reaction to significantly increase the polymerization activity and improves the grain morphology. The pre-activation of the metallocene compound is carried out in solution. The metallocene is preferably dissolved in a solution of the aluminoxane in an inert hydrocarbon. Suitable inert hydrocarbons are aliphatic and aromatic hydrocarbons. Toluene is preferred.

The concentration of the aluminoxane in the solution is in the range from about 1% by weight to the saturation limit, preferably from 5 to 30% by weight, in each case based on the solution as a whole. The metallocene can be employed in the same concentration, but is preferably employed in an amount of from $10^{-4}$ to 1 mol per mol of aluminoxane. The pre-activation time may be 5 minutes to 60 minutes. The reaction is carried out at a temperature of from −78C to 100C, preferably from 0C to 70C. The metallocene can also be pre-polymerized or applied to a support. Pre-polymerization is preferably carried out using an olefin to be polymerized. Examples of suitable supports are silica gels, aluminum oxides, solid aluminoxane or other inorganic support materials. Another suitable support material is a polyolefin powder in finely divided form.

According to the invention, compounds of the formulae $R_xNH_{4-x}BR'_4, R_xPH_{4-x}BR'_4, R_3CBR'_4$ or $BR'$ can be used as suitable cocatalysts instead or in addition to an aluminoxane. In these formulae, x is a number from 1 to 4, preferably 3; the radicals R are identical or different, preferably identical, and are $C_1$–$C_6$ alkyl, or $C_6$–$C_{18}$ aryl or 2 radicals R, together with the atom connecting them, form a ring; and the radicals R' are identical or different, preferably identical, and are $C_6$–$C_{18}$ aryl, which may be substituted by alkyl, haloalkyl or fluorine. In particular, R is ethyl, propel, butyl or phenyl, and R' is phenyl, pentafluorophenyl, 3,5-bistrifluoromethylphenyl, mesityl, xylol or tolyl. (See EPA 277 003, EPA 277 004 and EPA 426 638).

When the above-mentioned cocatalysts are used, the actual (active) polymerization catalyst comprises the product of the reaction of the metallocene and the involved co-catalyst. For this reason, this reaction product is preferably prepared first outside the polymerization reactor in a separate step using a suitable solvent. In principle, suitable cocatalysts are according to the invention any compounds which, due to their Lewis acidity, are able to convert the neutral metallocene into a cation and stabilize the latter ("labile coordination"). In addition, the cocatalyst or the anion formed therefrom should not undergo any further reactions with the metallocene cation formed.

In order to remove catalyst poisons present in the olefin, purification by means of an alkylaluminum compound, for example, $AlMe_3$ or $AlEt_3$, is advantageous. The purification may be carried out in the polymerization system itself. Alternatively, the olefin may be brought into contact with the aluminous compound before addition to the polymerization system.

Polymerization Process

Olefin polymerization or copolymerization in the presence of a Formula III metallocene and a cocatalyst may be carried out in known manner in solution, in suspension or in the gas phase, continuously or batchwise, in one or more steps, at a temperature of from −60C to 200C, preferably from 30C to 80C. The polymerization or copolymerization is carried out using olefin of the formula $R^a$—CH═CH—$R^b$. In this formula, $R^a$ and $R^b$ are identical or different, and are a hydrogen atom or any alkyl radical preferably having 1 to 14 carbon atoms. However, $R^a$ and $R^b$, together with the carbon atoms connecting them, may alternatively form a ring. Examples of such olefins are ethylene, propylene, 1-butene, 1-hexene, 4-methyl-1-pentene, 1-octene, norborene and norbonadiene. In particular, propylene and ethylene are polymerized.

Hydrogen may be added as molecular weight regulator to increase the activity. The overall pressure in the polymerization system is 0.5 to 100 bar. The polymerization is preferably carried out in the industrially relevant pressure range of from 5 to 64 bar.

The metallocenes of this invention may be used as polymerization catalysts in a concentration, based on the transition metal, of for $10^{-3}$ to $10^{-8}$ mol, preferably from $10^{-4}$ to $10^{-7}$ mol, of transition metal per $dm^3$ of solvent or per $dm^3$ of reactor volume. The aluminoxane may be used in a concentration of from $10^{-5}$ to $10^{-1}$ mol. preferably from $10^{-4}$ to $10^{-2}$ mol, per $dm^3$ of solvent per $dm^3$ of reactor volume. The other cocatalysts mentioned may be used in approximately equimolar or greater amounts with respect to the metallocene.

If the polymerization is carried out as a suspension or solution polymerization, a conventional inert solvent is used. For example, the process may be carried out in an aliphatic or cycloaliphatic hydrocarbon, such as propane, butane, pentane, hexane, heptane, isoctaine, cyclohexane and methylcyclohexane. Alternatively, benzene, toluene or hydrogenated diesel oil fraction may be used as a solvent.

The polymerization is preferably carried out in the liquid monomer. If inert solvents are used, the monomers are metered in as gases or liquids.

The polymerization may have any desired duration. Specific examples of metallocenes which may be included in the invention are compounds having the formula I or formula II in which all R groups are methyl groups and in which Z is a dialkyl, silyl or —$(CH_2)_n$— (n=1–4).

EXEMPLIFICATION OF THE INVENTION

EXAMPLE 1

Synthesis of 2-Methyl-4-(2,6-Dimethylphenyl)Indene

Reaction

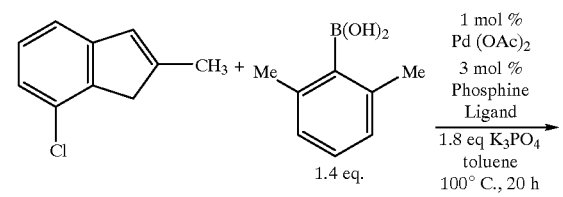

7
-continued

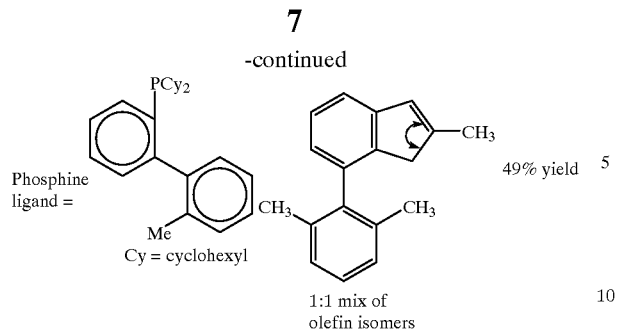

Phosphine ligand =

Cy = cyclohexyl

49% yield

1:1 mix of olefin isomers

Procedure

A flask is charged with palladium (II) acetate (18.5 mg, 0.08 mmol), 2-(dicyclohexylphosphino)-2'-methyl biphenyl (94 mg, 0.26 mmol), (2,6-dimethylphenyl) boronic acid (1.7 g, 11.3 mmol, freshly recrystallized from Et$_2$O/hexane) (synthesized according to literature, *J.Am.Chem.Soc.* (1960) 82:3053–3059), and potassium phosphate (3.1 g, 14.6 mmol). The flask is filled with nitrogen before addition of dry deoxygenated toluene (14 mL) and 2-methyl-4-chloroindene (1.3 g, 7.9 mmol) (synthesized according to U.S. Pat. No. 5,789,634) via syringe under nitrogen. The mixture was stirred at 100° C. for 20 hours under nitrogen. Analysis of an aliquot by GC/MS revealed a 66% yield of desired product and 33% of starting 2-methyl-4-chloroindene. The reaction was cooled to ambient temperature, diluted with diethyl ether and washed with aqueous saturated sodium bicarbonate. The organic phase was dried over sodium sulfate, filtered and evaporated in vacuo. The residue was purified by chromatography on silica gel eluted with hexane to afford 0.9 grams (49% isolated yield) of 2-methyl-4-(2,6-dimethylphenyl)indene as a pale yellow waxy solid, a 1:1 mixture of the two olefin isomers by proton NMR. Data: TLC Rf0.3 (hexane); observed M$^+$ 234, calculated 234; $^1$H NMR (250 MHz, CD$_2$Cl$_2$) 7.35–7.13 (m, 5H), 6.96 (d, 0.5H), 6.84 (d, 0.5H), 6.81 (dd, 0.5H), 5.99 (br t, 0.5 H), 3.39 (s, 1H), 2.89 (s, 1H), 2.09 (s, 3H), 1.97 (s, 6H).

This procedure uses 1 mol % Pd(OAc)2 and 3 mol % phosphine ligand, 1.4 equivalents of the boronic acid and 1.8 equivalents of potassium phosphate relative to chloroindene substrate.

EXAMPLE 2

Preparation of 2-Methyl-4-(2,6-dimethylphenyl) Indene from 2-Methyl-4-Bromoindene A flask is charged with palladium (II) acetate (60.8 mg, 0.27 mmol), 2-(dicyclohexylphosphino)-biphenyl (321 mg, 0.9 mmol), (2,6-dimethylphenyl) boronic acid (1.0 g, 6.6 mmol), and potassium phosphate (2.3 g, 10.8 mmol). The flask is filled with nitrogen before addition of dry deoxygenated toluene (14.8 g) and 2-methyl-4-bromoindene (1.0 g, 4.7 mmol) (prepared in analogous fashion to 2-methyl-4-chloroindene) via syringe. The mixture was stirred at 87–95° C. for 20 hours under nitrogen. Analysis of an aliquot by GC/MS revealed a 67% yield of desired product and 32% of starting 2-methyl-4-bromoindene. Work up and purification as described in Example 1 provided a 55% yield of 2-methyl-4-(2,6-dimethylphenyl) indene as 1:1 mixture of two olefin isomers. MS observed 234.

COMPARATIVE EXAMPLE 3

When 2-methyl-4-chloroindene is reacted with 2,6-dimethylphenyl magnesium bromide in the presence of Ni(dppp)Cl$_2$ as described in U.S. Pat. No. 5,789,634, GC/MS (gas chromatography/mass spectrometry) analysis shows that none of the 2-methyl-4-(2,6-dimethylphenyl) indene is produced.

EXAMPLE 4

Proposed Synthesis of Formula III Metallocenes

To a solution of 2 grams of 2-methyl-4-(2,6-dimethylphenyl) indene from Example 1 in 10 grams of diethyl ether at −30° C. and −40° C. and allowed to warm to ambient temperature and stirred for four hours. It is cooled to −30° C. and treated with 0.5 eq of dimethyldichlorosilane, and allowed to warm slowly, and stirred overnight. The solution of the resulting dimethylsilyl bridged ligand (Formula II) is cooled to −30° C. and 2 equivalents of 1.6 M BuLi are added. The reaction is warmed to ambient temperature and stirred overnight. The reaction is re-cooled to −40° C. and quickly 1 equivalent of solid ZrCl$_4$ is added. The reaction is allowed to warm to ambient temperature and stirred overnight. Remove bulk of ether by evaporation under reduced pressure. The solids are filtered and washed with hexane. The filter cake is slurried in dry dichloromethane and filtered through a pad of Celite. The pad and solids are extracted with dichloromethane. The dichloromethane is evaporated under reduced pressure, and the solids are crystallized using toluene to isolate the solid Formula III metallocene.

We claim:
1. A compound of (i) Formula I:

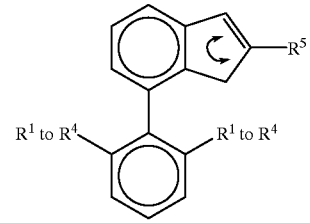

in which R$^1$, R$^2$, R$^3$, R$^4$, and R$^5$ are identical or different hydrocarbyl groups, and in which the symbol ⊂ indicates a shift in the position of the double bond;

or (ii) Formula II:

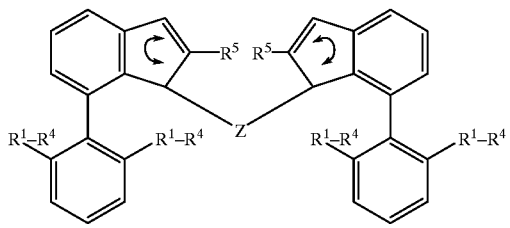

in which R$^1$ to R$^5$ are as described in Formula I, and Z is a bridge.

2. A compound of Formula I

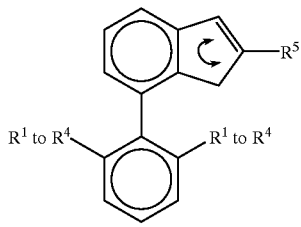

as set forth in claim 1 wherein not more than one of $R^1$ to $R^4$ is aryl.

3. A compound of Formula I

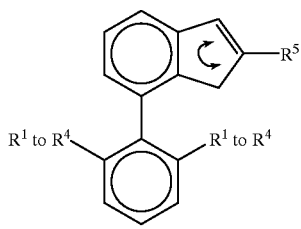

as set forth in claim 1 wherein each of $R^1$ to $R^5$ is any alkyl group which may be the same as or different from any other $R^1$ to $R^5$ group.

4. A compound of Formula I

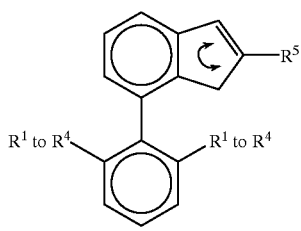

as set forth in claim 1 wherein each of $R^1$ to $R^5$ is any $C_1$ to $C_6$ alkyl group which may be the same as or different from any other $R^1$ to $R^5$ group.

5. A compound of Formula I

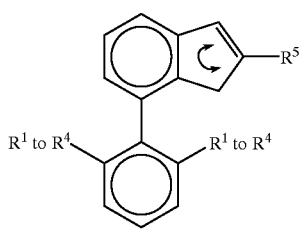

as set forth in claim 1 wherein each of $R^1$ to $R^5$ is methyl.

6. 2-alkyl-4-(2,6-dialkylphenyl) indene.

7. 2-methyl-4-(2,6-dimethylphenyl) indene.

8. A compound of Formula II

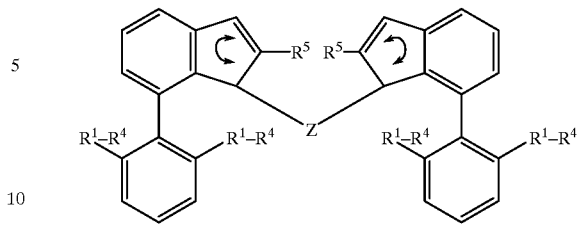

as set forth in claim 1 wherein each of $R^2$, $R^3$ and $R^5$ is any alkyl group which may be the same as or different from any other $R^2$, $R^3$ or $R^5$ group.

9. A compound of Formula II

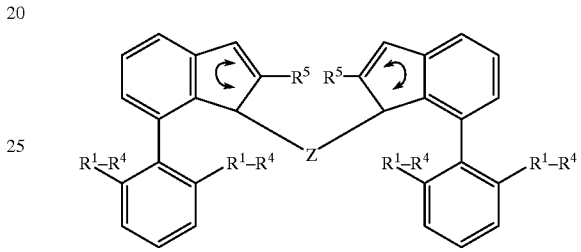

as set forth in claim 1 wherein each of $R^2$, $R^3$ and $R^5$ is any $C_1$ to $C_6$ alkyl group which may be the same as or different from any other $R^1$ to $R^5$ group.

10. A compound of Formula II

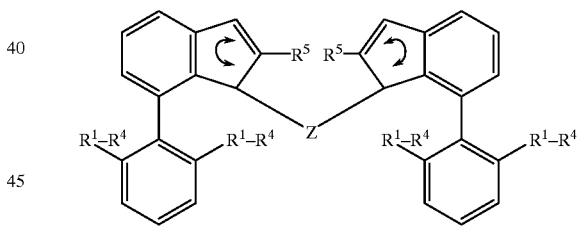

as set forth in claim 1 wherein each of $R^2$, $R^3$ and $R^5$ is methyl.

11. A compound of Formula II

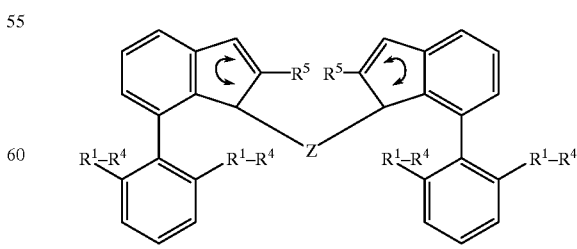

as set forth in claim 1 wherein Z is a dialkyl silyl bridge.

12. A compound of Formula II

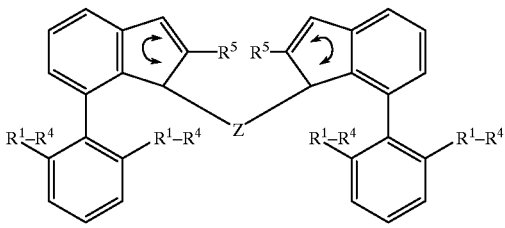

as set forth in claim 1 wherein Z is a hydrocarbon bridge.

13. A method for the synthesis of a compound of Formula I of claim 1 which comprises converting a 2-alkyl-4—$\underline{X}$ indene to said compound of Formula I by treatment with organometallic compound effective to produce by cross-coupling said Formula I compound from said 2-alkyl-4—$\underline{X}$ indene wherein —X— is a halogen or a triflate.

14. A method for the synthesis of a compound of Formula I in claim 1 which comprises treating a 2-alkyl-4—$\underline{X}$ indene, wherein X is halogen or triflate with an organometallic compound having the formula

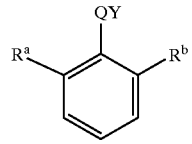

wherein $R^a$ and $R^b$ are alkyl groups, Q is magnesium, tin, silicon or zinc, and Y is any halogen or triflate, a $C_1$ to $C_6$ trialkyl silicon, a $C_1$ to $C_6$ trialkyl tin, a phenyl boronic group or a zinc halide.

15. The method of claim 14 wherein said synthesis is conducted in the presence of a cross-coupling catalyst.

16. The method of claim 15 method wherein said cross-coupling catalyst is a metal compound having a phosphine liquid.

17. The method of claim 15 wherein said metal compound is a nickel or a palladium compound.

18. The method of claim 14 wherein said cross-coupling catalyst is Ni(dppp)Cl$_2$ (nickel diphenylphosphino propane dichloride), Ni(PPh$_3$)$_2$Cl$_2$, Pd(PPh$_3$)$_4$, X$_2$Pd(PPh$_3$)$_2$ (X=halogen), Cl$_2$Pd(dppf) (dichloro palladium diphenylphosphino ferrocene) or combination of Pd(OAc)$_2$ (palladium acetate) or Pd$_2$dba$_3$ (in which dba is dibenzylidene acetone) with phosphine PR$_3$, PAr$_3$, or PR$_2$Ar where R is a $C_1$ to $C_6$ alkyl group and Ar is a $C_6$ to $C_{10}$ aryl group.

19. The method of claim 14 wherein said treating occurs in the presence of a non-interfering solvent.

20. The method of claim 14 wherein said treating occurs in the presence of an ether or an aromatic hydrocarbon solvent.

21. The method of claim 20 wherein said solvent is ethyl ether, tetrahydrofuran, dioxane, dimethoxyethane, benzene, toluene or a xylene.

22. The method which comprises converting a compound of Formula I of claim 1 into a compound of Formula II of claim 1, wherein said converting is accomplished by treating said compound of Formula I with an alkali metal alkyl and a bridging agent.

* * * * *

UNITED STATES PATENT AND TRADEMARK OFFICE
CERTIFICATE OF CORRECTION

PATENT NO.    : 6,291,699 B1
DATED         : September 18, 2001
INVENTOR(S)   : John M. Birmingham et al.

It is certified that error appears in the above-identified patent and that said Letters Patent is hereby corrected as shown below:

Column 2,
Lines 18 and 55, delete "symbol z,, 900" and insert -- symbol  --.

Signed and Sealed this

Sixth Day of August, 2002

Attest:

JAMES E. ROGAN
Attesting Officer    Director of the United States Patent and Trademark Office

Disclaimer 6,291,699 — John M. Birmingham, Longmont; Sandra Russo-Rodriguez, Superior, both of CO (US). 2-ALKYL-4-(2,6-DIALKYLPHENYL) INDENES. Patent dated September 18, 2001. Disclaimer filed June 24, 2002, by the assignee, Boulder Scientific Company.

Hereby enters this disclaimer to claims 8, 9 and 10 of said patent.

*(Official Gazette, August 26, 2003)*